United States Patent
Matthews et al.

(10) Patent No.: US 10,555,519 B2
(45) Date of Patent: Feb. 11, 2020

(54) NON-TOXIC LARVICIDE

(71) Applicants: Scott Matthews, Wilmington, NC (US); Ravi Durvasula, Albuquerque, NM (US); Ivy Foo-Hurwitz, Albuquerque, NM (US)

(72) Inventors: Scott Matthews, Wilmington, NC (US); Ravi Durvasula, Albuquerque, NM (US); Ivy Foo-Hurwitz, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 20 days.

(21) Appl. No.: 15/567,106

(22) PCT Filed: Apr. 18, 2016

(86) PCT No.: PCT/US2016/028141
§ 371 (c)(1),
(2) Date: Oct. 17, 2017

(87) PCT Pub. No.: WO2016/168837
PCT Pub. Date: Oct. 20, 2016

(65) Prior Publication Data
US 2018/0098535 A1  Apr. 12, 2018

Related U.S. Application Data

(60) Provisional application No. 62/148,774, filed on Apr. 17, 2015, provisional application No. 62/289,394, filed on Feb. 1, 2016, provisional application No. 62/294,174, filed on Feb. 11, 2016.

(51) Int. Cl.
*A01N 25/28* (2006.01)
*A01N 65/00* (2009.01)

(52) U.S. Cl.
CPC ............. *A01N 25/28* (2013.01); *A01N 65/00* (2013.01)

(58) Field of Classification Search
None
See application file for complete search history.

(56) References Cited

U.S. PATENT DOCUMENTS

| 2006/0165614 A1* | 7/2006 | Nelson .................. A61K 9/5068 424/50 |
| 2007/0042182 A1 | 2/2007 | Markus et al. |
| 2008/0166415 A1 | 7/2008 | Markus et al. |

FOREIGN PATENT DOCUMENTS

| CA | 1163496 A1 * | 3/1984 | |
| EP | 0242135 B1 | 7/1990 | |
| KR | 2016009747 * | 1/2016 | |
| WO | 199319622 A2 | 10/1993 | |
| WO | WO-02056709 A1 * | 7/2002 | ............. A23D 9/007 |
| WO | WO-2007063268 A1 * | 6/2007 | ............. A01N 31/02 |
| WO | 2013113577 A1 | 8/2013 | |
| WO | WO-2014080199 A2 * | 5/2014 | ............. A01N 25/28 |

OTHER PUBLICATIONS

Weston(Anal Burning and Peppermint oil) Postgrad. Med. J., vol. 63, No. 742, 717, 1987) (Year: 1987).*
Papathanasopoulos et al.(Effect of Peppermint oil on Gastric Accommodation to a Meal, Compliance and Sensitivity to Balloon Distension in Health, Gastroenterology, 2011, vol. 140 No. 5, Suppl. 1 pp. S811) (Year: 2011).*
Heaney et al.(Real time monitoring of exhaled volatiles using atmospheric pressure chemical ionization on a compact mass spectrometer, Bioanalysis, 2016, vol. 8 No. 13, 1325-1336) (Year: 2016).*
Hebert et al.(Comparison of the toxicity of cinnamaldehyde when administered by microencapsulation in feed or by corn oil gavage, Food and Chemical Toxicology, 1994, 32(12), 1107-15) (Year: 1994).*
Beauchamp et al.(Real time breath gas analysis for pharmacokinetics: monitoring exhaled breath by on line proton-transfer-reaction mass spectrometry after ingestion of eucalyptol-containing capsules; J. of Breath Research, 2010, 4(2)) (Year: 2010).*
Schaffarczyk et al.(Syntheses of chiral 1,8-Cineole metabolites and determination of their enantionmeric composition in Human Urine after ingestion of 1,8-cineole containing capsules, ChemPlusChem, 2013, 78(1), 7785) (Year: 2013).*
Beauchamp et al.(Time-dependent aroma changes in breast milk after oral intake of a pharmacological preparation containing 1,8-cineole, Clinical Nutrition, 2012, 31(5), 682-692) (Year: 2012).*
Mulyani et al. Synthesis and characterization of silica-lavender microencapsulation by sol gel-emulsion method for anti mosquito textile, Advanced Materials Research (Durnten-Zurich, Switzerland) (2013), 789(Advances in Materials, Processing and Manufacturing), (Year: 2013).*

* cited by examiner

*Primary Examiner* — Alton N Pryor
(74) *Attorney, Agent, or Firm* — Gonzales Patent Services; Ellen M. Gonzales

(57) ABSTRACT

An larvicide comprising an essential oil encapsulated within a non-viable yeast cell. The larvicide is particularly effective against mosquito larvae, non-toxic to humans and other non-target species, inexpensive to make, and non-toxic during manufacture, transport, and storage.

20 Claims, No Drawings

NON-TOXIC LARVICIDE

CROSS-REFERENCE TO RELATED APPLICATIONS

The following application claims benefit of U.S. Provisional Application Nos. 62/148,774, filed Apr. 17, 2015, 62/289,394, filed Feb. 1, 2016, and 62/294,174, filed Feb. 11, 2016, each of which is hereby incorporated by reference in its entirety.

BACKGROUND

Various insects are known carriers for pathogens of human and/or non-human disease and/or are linked to the destruction of crops and/or other undesired outcomes. Thus, significant resources are devoted to limiting and/or controlling various "pest" insect populations. For example, mosquitos are known carriers for pathogens of diseases including, but not limited to, malaria (*Anopheles*) Zika virus, dengue virus, yellow fever, (*Aedes*) and West Nile virus (*Culex*). Accordingly, it is very desirable to kill pest insects like mosquitos at the larval stage, before they can spread disease and infection.

Unfortunately the most commonly used method for limiting and/or controlling undesirable insect populations are pesticides which are often harmful to humans and other non-target species. In the case of mosquitos and other water born pests, many communities resort to adding synthetic pesticides to water reservoirs, including sources of potable water, for mosquito control. The synthetic pesticides used are neurotoxins and growth inhibitors. Their dispersal in the water supply poses a risk to these communities. Furthermore, the manufacture, storage and transport of chemical pesticides all present potential hazards to humans, animals, and/or other non-target species.

Other methods for controlling insect populations, such as the engineering of genetically modified insects are expensive and currently available in only limited areas and only for a specific variety of mosquito (*Aedes*). Furthermore, because it is not always possible to control the movement or migration of an insect population, genetic modification may not be a viable mechanism for populations that are considered pests in a particular region, but which are benign or even beneficial in other regions. Furthermore, because this technology is new and largely untested, it's difficult to predict the long-term consequences and efficacy of releasing genetically modified populations of mosquitos.

Accordingly, novel methods of controlling pest insect populations that are non-toxic to humans, animals, and/or desirable insect populations are thus desirable. However, while non-toxic (to human and other animals) substances such as essential oils have been shown to be effective in killing insect larvae, deployment of essential oils to pest populations is problematic, as large amounts of essential oil would have to be repeatedly added to oviposition sites to achieve significant reduction in the pest population. Furthermore, the dispersed oils would then be vulnerable to degradation by UV radiation and would disrupt the aquatic environment, with the potential for adverse effects on non-target species. Accordingly, an effective mechanism for delivering substances like essential oils directly to the pest larvae population is greatly desired.

It should thus be well understood that because insects are ubiquitous, often prevalent in poor and/or remote communities, and most negatively impact vulnerable populations, methods of controlling pest insects that are inexpensive, easy to manufacture, transport, store, and deploy, would be of great benefit.

SUMMARY

The present disclosure provides a novel insect larvicide that is non-toxic to humans and other non-target species, inexpensive to make, and non-toxic during manufacture, transport, and storage. No harmful waste products are generated during the manufacture of this larvicide and all of its components are generally regarded as safe. Moreover, larvicidal element is effective only when the larvicide is consumed by larvae of the pest insect. The present disclosure also provides method for making and using the novel larvicide.

DETAILED DESCRIPTION

The present disclosure provides a novel insect larvicide capsule that is non-toxic to humans and other non-target species, inexpensive to make, and non-toxic during manufacture, transport, and storage. Moreover, according to various embodiments, the larvicidal element is effective only when the capsule is consumed by the target larvae. The present disclosure also provides methods for making and using the novel larvicide.

For the purposes of the present disclosure the target larvae or target species refers to the intended target of the larvicide. While many of the specific embodiments provided herein refer to mosquito larvae as the intended target, it will be understood that larvae of other insects or other species may also be the intended target and that the larvicide may be altered, as described herein, to be more particularly suited towards one target or another. Furthermore, it will be understood that the novel larvicide described herein may be designed to be suitable for more than one target and that references to "a" or "the" target species does not necessarily preclude embodiments wherein there is more than one target species.

According to various embodiments, the novel larvicide capsule comprises a larvicidal element encapsulated in an ingestible delivery vehicle. According to various embodiments, the larvicidal element is a substance that is non-toxic to humans and other non-target species, but which negatively impacts the ability of the target species to behave in an undesirable manner. For example, contact between the larvicidal element and the target may result in the immediate or eventual death of the target. Alternatively, contact between the larvicidal element and the target may result in the larva being unable to transmit a disease vector, sterile, or developmentally hindered in some other way. According to a specific embodiment, the larvicidal element is an essential oil.

Essential oils include terpene components and are naturally produced by plants to provide protection from larvae and adult insects, while being non-toxic to humans. For the purposes of the present disclosure, essential oils are defined as terpene containing oils produced by plants. For more than three decades, essential oils have been recognized as cheap, effective larvicides. Essential oils are thought to exert larvicidal effects through three different mechanisms: neurotoxicity, growth inhibition, and interruption of metabolic pathways. The simultaneous action of these mechanisms retards the evolution of resistance to the larvicide. Examples of essential oils that are suitable for use as larvicidal elements include, but are not necessarily limited to lemongrass, thyme basil, cinnamon, peppermint, orange peel, and neem oils. Since the composition of essential oils varies, oils may be combined to enhance larvicidal efficacy where the environment or larval physiology provide opportunity. Suitable essential oils can be purchased commercially at low cost or extracted from the plants from which they are derived using standard techniques. As a specific example of an essential oil's known efficacy as a larvicide, lemongrass oil has been shown in laboratory studies to achieve 100% larval killing within twenty-four hours at concentrations of less than 50 ppm. Accordingly, in a more specific embodiment, the larvicidal element is or includes lemongrass oil.

For the purposes of the present disclosure the term "ingestible delivery vehicle" is intended to mean an entity capable of encapsulating the larvicidal element and generally sequestering it from the environment until the delivery vehicle is ingested by the target species. The ingestible delivery vehicle is generally non-toxic to non-target species. In general, the ingestible delivery vehicle should be attractive as a food source to the target species and have sufficient durability in the environment in which it will encounter the target species that it can withstand the conditions long enough to be ingested by the target species. For example, many larvae are water-borne and/or find nutrients in aquatic environments thus, in these circumstances the ingestible delivery vehicle should not readily degrade in an aquatic environment. According to some embodiments the ingestible delivery vehicle may be inert to all or most environments that do not replicate the environmental conditions found in the digestive system of the target species. Accordingly, to various embodiments, the ingestible delivery vehicle may be an inactive or non-viable yeast cell. According to a more specific embodiment, the ingestible delivery vehicle is a non-viable yeast cell of the *S. cerevisae* variety. It is a well-documented feature of larval biology that mosquito larvae will preferentially consume and readily digest *S. cerevisae*. In fact, a recommended food for rearing larvae in laboratory settings is *S. cerevisae*. Moreover, the cell membrane of yeast cells is rich in beta-6-glucan, a polysaccharide, and chitin. Larvae have intestinal enzymes specialized for the digestion of beta-6-glucan to obtain chitin and beta glucans and are able to rapidly break down ingested yeast cell membranes. Other suitable ingestible delivery vehicles may include (1) *S. cerevisae* genetically modified for greater essential oil loading and a thicker cell membrane and (2) *S. cerevisae* opsonized with fragments of adult insect exoskeleton, bacteria, corn oil, corn sugar, and other phagostimulant elements of the larval diet.

The larvicidal element may be encapsulated, infused, injected, entrapped, loaded, etc. (referred to herein collectively as "encapsulated" for ease of discussion) into the ingestible delivery vehicle using any suitable method depending on the specific larvicidal element and ingestible delivery vehicle being used. Examples of suitable methods for encapsulating the larvicidal element in the ingestible delivery vehicle include, but are not limited to, a combination of heat and agitation, plasmolyzation, and coacervation.

According to a specific embodiment wherein a larvicidal capsule comprises an essential oil such as lemongrass oil as the larvicidal element and a yeast cell such as an *S. cerevisae* cell as the ingestible delivery vehicle, the lemongrass oil can be encapsulated within the yeast cell via a process using heat and agitation, as described in greater detail in the Examples section below. The heat and agitation method results in the encapsulation of all components of the essential oils without discrimination, including terpenes and aldehydes. However, molecules as large as 400,000 can freely diffuse through the cell wall.

Once the essential oil enters the cell, the yeast becomes nonviable and cannot replicate, thereby reducing or eliminating any potential impact on the environment during storage, transportation, and/or use. However, while the yeast cell is nonviable, the cell's thick outer membrane remains intact and thus sequesters the oil from the surrounding environment. In fact, after encapsulation, water/ethanol extraction is the only non-enzymatic laboratory for removing the encapsulated oil. As explained above, some target species, such as mosquito larvae have intestinal enzymes that are specialized for the digestion of beta-7-glucan, thus resulting in a system wherein the lemongrass oil/yeast cell capsule is essentially inert to all environments it is likely to encounter other than the specialized digestive systems of the target mosquito larvae. Furthermore, it should be noted that both yeast and lemongrass oil are commonly found in food and are entirely harmless to humans.

According to a specific embodiment of use, the larvicidal capsules of the present disclosure could be distributed via (1) an air-water displacement propulsion device to oviposition sites or (2) an auto-dissemination strategy using a cornstarch-based powdered distributed at nesting sites. The larvae then consume the larvicidal capsules and the yeast cell wall is broken down by enzymes in the gut of $3^{rd}$ and $4^{th}$ larval instars, which liberates the essential oil(s) from the capsule, allowing the oil to act on the larvae, resulting in larval death. In general this system could be used in additional to or instead of existing municipal or rural larvicide/insecticide/other pest control programs. Furthermore, because the presently described system can be used in environments where traditional chemical larvicides and insecticides aren't used due to safety risks, the presently described larvicidal system can be used in high-value breeding sites, including in drinking water reservoirs and the like. Alternatively, as described in greater detail below, the larvicidal capsule may be designed to piggy back female mosquitos, who then carry the capsules back to oviposition sites.

Accordingly, the present disclosure provides methods for delivering or directing the larvicide towards or retaining the larvicide in specific desired environments. For example, because the larvicide targets larvae, it may be desirable to direct and maintain the larvicide to oviposition environments so as to ensure the larvae will have the opportunity to encounter and ingest the larvicide. According to some embodiments, this may involve modifying the larvicidal capsule.

For example, as stated above, the larvicidal capsule may be incorporated in a powder to piggy back on female mosquitos, who can then carry the capsules to known or unknown oviposition sites. For example, the *A. Aegypti* mosquito tends to rest in dry, sheltered areas such as residential awnings and holes in trees, but also tend to visit many oviposition sites. Accordingly, rather than trying to place the larvicide at each oviposition site, it may be easier to place the larvicide in known resting sites or areas that look like likely resting sites. The larvicidal capsules of the present disclosure may be coated with silica, cornstarch or another pH ~7 soluble coating to produce a powder which can be spread at likely resting sites and which can then be picked up and delivered to oviposition sites by female mosquitos. Moreover, anatomical difference between male and gravid female mosquitoes could be exploited to improve targeting and transfer of the larvicide to the oviposition sites. For example, the soluble coating may be able to accommodate biofunctionalization for tuning adherence to and aquatic release from female mosquitoes. Soluble coatings may provide other advantages including increasing the effective lifespan of the larvicide and or increasing the speed and efficacy of distribution.

As another example of possible larvicidal capsule modifications, the larvicidal capsules of the present disclosure may be modified to achieve certain desired buoyancies. For example, mosquito larvae are know to have different feeding behaviors, i.e. some are surface feeders while others are benthic (bottom) feeders. In order to ensure that the larvicide reaches the different feeding populations, the present disclosure provides methods for producing capsules with different buoyancies, allowing the capsules to maintain different water levels, or to maintain the location of the capsules in, for example, moving or running water bodies.

According to an embodiment, the buoyancy of the capsule can be altered by introducing air pockets in the capsule. For example, when the ingestible delivery vehicle is a non-viable yeast cell, air pockets could be introduced into the yeast membranes during the encapsulation stage via oxygen infusion. In general, by controlling the volume of the air pocket in relationship to the density of the contents of the capsule, one can control the degree of buoyancy of the capsule, thereby producing a capsule that would float on the surface of the water or maintain a certain water depth.

Alternatively or additionally, the buoyancy of the capsule can be altered by applying an adhesive element to the exterior of the ingestible delivery vehicle. The presence of an adhesive element promotes clumping and facilitates sinking of the capsules. Suitable adhesive elements may take the form, for example of muco-adhesive compounds such as doped alginates. These could be applied to the exterior of the capsules by painting, dipping, spraying, and immersion/vacuum drying.

Combinations of air pockets and adhesive elements could be used to even more precisely fine tune the capsule so that it can maintain a desired position within the water column. Additionally, buoyancy of the capsule may be altered by altering its essential oil loading capacity, e.g. through the use of plasmolyzers.

Alternative or additional modifications of the capsules include opsonization with phagostimulants, membrane saturation with chemoattractants, and combination in biodynamic configurations to facilitate larval feeding dynamics.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLES

Encapsulation of Lemongrass Oil in *S. Cerevisiae*

*S. cerevisae* as fresh or dried baker's yeast is heated and proofed for viability.

Lemongrass oil, heated *S. cerevisiae* and distilled water are combined in a 1:2.5:4 volumetric ratio (Mixture 1).

Mixture 1 is agitated in a rotary incubator at 100 rpm and 40 C. for a minimum of 4 hours.

Mixture 1 is transferred to vials and centrifuged for 10 minutes at 2000×g.

After decanting supernatant oil and water into beaker for later analysis, cells are washed 5 times with corn oil, Cells are dried for 1 hour at 250 F. in a vented or vacuum drying oven.

Cells are washed 5× with corn oil.

Cells are dried for 2 hours at 250 F. in a vented or vacuum drying oven.

Cells not scheduled for immediate use may be freeze-dried for 48 hours.

Efficacy of Encapsulated Lemongrass Oil Larvicide

Protocol

Third and fourth instar larvae are collected following a starvation period.

Experimental and control groups (25 larvae per group) allowed to accommodate to 100 ml-200 ml distilled water in enamel bowls for 1 hour.

Experimental group fed essential oil micro-encapsulations, four replicates per concentration.

Test containers are maintained at 25=28 C., with 12/12 light/dark environment preferred.

Mortality after 24 and 48 hours with no additional nutrition

Determination of 50% and 90% mortality and inhibition of adult emergence concentrations.

Abbott's test: control vs. experimental mortality

What is claimed is:

1. A larvicidal capsule comprising an essential oil encapsulated in a non-viable yeast cell and wherein the larvicidal capsule is coated with a soluble silica coating.

2. The larvicidal capsule of claim 1 wherein the essential oil is lemongrass oil.

3. The larvicidal capsule of claim 1 further comprising a mechanism for maintaining a desired position within a body of water.

4. The larvicidal capsule of claim 3 wherein the mechanism for maintaining a desired position within a body of water is a buoyancy control mechanism.

5. The larvicidal capsule of claim 4 wherein the buoyancy control mechanism comprises an air pocket within the non-viable yeast cell.

6. The larvicidal capsule of claim 5 wherein the air pocket maintains the larvicidal capsule on the surface of the body of water.

7. The larvicidal capsule of claim 5 wherein the air pocket maintains the larvicidal capsule below the surface of the body of water but above the bottom of the body of water.

8. The larvicidal capsule of claim 3 wherein the mechanism for maintaining a desired position within a body of water is an adhesive element that facilitates clumping of multiple larvicidal capsules.

9. The larvicidal capsule of claim 8 wherein the adhesive element is applied to the exterior of the non-viable yeast cell.

10. The larvicidal capsule of claim 5 further comprising an adhesive element that facilitates clumping of multiple larvicidal capsules.

11. A method for forming a larvicidal capsule comprising encapsulating an essential oil within a non-viable yeast cell and wherein the larvicidal capsule is coated with a soluble silica coating.

12. The method of claim 11 wherein the essential oil is lemongrass oil.

13. The method of claim 11 further comprising introducing a buoyancy control mechanism into the larvicidal capsule.

14. A larvicidal capsule comprising an essential oil encapsulated in a non-viable yeast cell and wherein the larvicidal capsule is coated with a soluble silica coating, wherein the ingestible delivery vehicle further comprises a buoyancy control mechanism that maintains the larvicidal capsule at a desired buoyancy.

15. The larvicidal capsule of claim 14 wherein the buoyancy control mechanism is an air pocket.

16. The larvicidal capsule of claim 14 wherein the buoyancy control mechanism maintains the larvicidal capsule on the surface of the body of water.

17. The larvicidal capsule of claim 14 wherein the buoyancy control mechanism maintains the larvicidal capsule below the surface of the body of water but above the bottom of the body of water.

18. The larvicidal capsule of claim 14 wherein the buoyancy control mechanism is an adhesive element that facilitates clumping of multiple larvicidal capsules.

19. The larvicidal capsule of claim 18 wherein the adhesive element is applied to the exterior of the non-viable yeast cell.

20. The larvicidal capsule of claim 14 wherein the essential oil is lemongrass oil.

* * * * *